United States Patent
Evans et al.

(10) Patent No.: US 6,627,205 B2
(45) Date of Patent: *Sep. 30, 2003

(54) OVO VACCINATION AGAINST COCCIDIOSIS

(75) Inventors: Nigel A. Evans, East Lyme, CT (US); Robert Craig Findly, Wethersfield, CT (US); Frederick H. Weber, Terre Haute, IN (US)

(73) Assignee: Pfizer Incorporated, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/094,087

(22) Filed: Mar. 8, 2002

(65) Prior Publication Data

US 2002/0090378 A1 Jul. 11, 2002

Related U.S. Application Data

(63) Continuation of application No. 08/973,151, filed as application No. PCT/IB95/00445 on Jun. 7, 1995, now Pat. No. 6,495,146.

(51) Int. Cl.[7] .................... A61K 39/012; A61K 39/002; A61K 39/00; A61K 39/38; C12N 1/12

(52) U.S. Cl. ................... 424/267.1; 424/184.1; 424/93.1; 424/265.1; 424/271.1; 435/252.1

(58) Field of Search ..................... 424/93.1, 184.1, 424/265.1, 267.1, 271.1; 435/252.1

(56) References Cited

U.S. PATENT DOCUMENTS

| | | |
|---|---|---|
| 4,040,388 A | 8/1977 | Miller |
| 4,301,148 A | 11/1981 | Shibata et al. ............... 424/93 |
| 4,357,320 A | 11/1982 | Apontowell et al. ......... 424/89 |
| 4,438,097 A | 3/1984 | Shirley |
| 4,458,630 A | 7/1984 | Sharma et al. ............... 119/1 |
| 4,469,047 A | 9/1984 | Miller ........................... 119/1 |
| 4,500,638 A | 2/1985 | Apontowell et al. ....... 435/235 |
| 4,505,892 A | 3/1985 | Apontowell et al. ......... 424/89 |
| 4,544,548 A | 10/1985 | Davis et al. |
| 4,593,646 A | 6/1986 | Miller et al. |
| 4,650,676 A | 3/1987 | Schenkel et al. ............ 424/88 |
| 4,681,063 A | 7/1987 | Hebrank |
| 4,735,801 A | 4/1988 | Stocker ....................... 424/92 |
| 4,751,079 A | 6/1988 | Burger et al. ................ 424/89 |
| 4,808,404 A | 2/1989 | Bhogal ......................... 424/88 |
| 4,935,007 A | 6/1990 | Bafundo et al. |
| 5,004,607 A | 4/1991 | Ragland et al. .............. 424/88 |
| 5,006,341 A | 4/1991 | Davis et al. ................. 424/442 |
| 5,028,421 A | 7/1991 | Fredericksen et al. ..... 424/85.2 |
| 5,055,292 A | 10/1991 | McDonald et al. |
| 5,068,104 A | 11/1991 | Bhogal et al. ................ 424/88 |
| 5,106,617 A | 4/1992 | Federicksen et al. ...... 424/85.2 |
| 5,279,960 A | 1/1994 | Anderson et al. .......... 435/243 |
| 5,288,845 A | 2/1994 | Chakraborty et al. .... 536/24.32 |
| 5,311,841 A | 5/1994 | Thaxton ...................... 604/51 |
| 5,339,766 A | 8/1994 | Phelps et al. ............... 119/6.8 |
| 5,359,050 A | 10/1994 | Chakraborty et al. .... 536/24.32 |
| 5,661,015 A | 8/1997 | Binger et al. |
| 5,674,484 A | 10/1997 | Miller et al. |
| 5,807,551 A | 9/1998 | Reynolds |
| 5,843,722 A | * 12/1998 | Bumstead et al. |
| 5,846,527 A | * 12/1998 | Miller et al. |
| 5,932,225 A | * 8/1999 | Wallach et al. |
| 6,019,985 A | 2/2000 | Brown et al. |
| 6,231,871 B1 | 5/2001 | Coloe |
| 6,306,385 B1 | * 10/2001 | Lee |
| 6,495,146 B1 | * 12/2002 | Evans et al. |
| 6,500,438 B2 | * 12/2002 | Evans et al. |
| 2002/0031530 A1 | * 3/2002 | Evans et al. |
| 2002/0090378 A1 | * 7/2002 | Evans et al. |
| 2002/0146435 A1 | * 10/2002 | Evans et al. |

FOREIGN PATENT DOCUMENTS

| | | |
|---|---|---|
| CA | 2098773 | 12/1994 |
| EP | 047662 | 12/1987 |
| EP | 256878 | 2/1988 |
| EP | 258045 | 3/1988 |
| EP | 291173 | 11/1988 |
| EP | 344808 | 12/1989 |
| EP | 109942 | 3/1991 |
| EP | 439056 | 7/1991 |
| EP | 522482 | 1/1993 |
| EP | 650733 | 5/1995 |
| JP | 4932381 | 9/1979 |
| JP | 2573189 | 4/1988 |
| JP | 1313437 | 12/1989 |
| NL | 8802399 | 4/1990 |
| WO | WO 9301276 | 1/1993 |
| WO | WO 9416725 | 8/1994 |
| WO | WO 96/40233 | * 12/1996 |
| WO | WO 9640234 | 12/1996 |
| WO | WO 9712582 | 4/1997 |
| WO | WO 9814212 | 4/1998 |
| WO | WO 8808699 | 11/1998 |

OTHER PUBLICATIONS

Ahmad, J. et al. Evaluation of a Modified–Live Virus Vaccine Administered in Ovo to Protect Chickens Against Newcastle Disease, *Am. J. Vet. Res.* 153(11): 1999–2001 (1992).

Jeffers, et al., Embryonic Response to Eimeria Tenella Infection *J. Parisitol.*, 56(4), 1970, 656–662.

Fredericksen, et al., *In Ovo Administration of a Potential Recombinant Coccidial Antigen Vaccine in Poultry* Les Colloques De L'Inra, 49,1989, 655–660.

(List continued on next page.)

Primary Examiner—Nita Minnifield
(74) Attorney, Agent, or Firm—Myers Bigel Sibley & Sajovec, P.A.

(57) ABSTRACT

The invention relates to a method of vaccinating a domesticated bird against coccidiosis comprising administering in ovo an effective immunizing dose of live Eimeria sporocysts or oocysts, or a mixture thereof.

28 Claims, No Drawings

OTHER PUBLICATIONS

Perkins, Microscopic Anatomy of Invertebrates vol. 1: Protozoa, Chap. 4: "Sporozoa", 261–331, 1991, Wiley–Liss.

Proceedings of the $VI_{TH}$ International Coccidosis Conference, Jun. 21–25, 1993, Guelph, Ontario, Canada, Univ. of Guelph; p. 103, Vaccine Symposium Papers.

Olson, *In Situ Enzyme–Linked Immunosorbent Assay to Quantitate in Vitro Development of Eimeria Tenella* Antimicrob. Agents Chemother., 34(7), Jul. 1990, 1435–39;.

Sharma & Burmester, *Resistance to Marek's Disease at Hatching in Chickens Vaccinated as Embryos with Turkey Herpesvirus* Avian Diseases, 26(1), 134–148.

Hosek, et al., *Improved Method for High–Yield Exystation and Purification of Infective Sporozoites of Eimeria SPP.* J. Protozool., 35(4), 1988, 583–589.

Schmatz, et al., *Purification of Eimeria Sporozoites by DE–SZ Anion Exchange Chromatography* J. Protozool., 31(1), 1984, 181–183.

Stedman's Medical Dictionary, $25^{th}$ ED., 1990, p. 947, 1087, 1457 and 1458.

Ruff, et al., Poultry Science, 1988, 67 (Supplement I):147.

Shirley; Live Vaccines for the Control of Coccidiosis; Vith International Coccidiosis Conference, p. 61–72 (1993).

Shirley; Development of a Live Attenuated Vaccine Against Coccidiosis of Poultry; Parasite Immunology; p. 117–124 (1989).

Watkins, et al.; The Effect of in Ovo Oocyst or Sporocyst Inoculation on Subsequent Coccidial Challenge; Vlth. International Coccidiosis Conference Abstract EL–2, Ontario, Canada (1993). Poultry Science 1597–1602 (1995).

R. B. Williams; The Development, Efficacy and Epidemiological Aspects of Paracox$^T$M, A New Coccidiosis Vaccine for Chickens; Mallinckrodt Veterinary LTD.; pp. 1–16 (1992).

\*\*Your Questions Answered; Live Attenuated Oral Coccidiosis Vaccine; Paracox, Cocci Vac®Vaccines, Cocci Vac®–T, Cocivac®–D, Cocci Vac®–B, Bursa–Vac®, Bursa–Vac®–3 and Bursa–Vac®–4; Mallinckrodt Veterinary.

\*\*The Headlines of the 80'S . . . Immucox; Coccivac Brand of Coccidiosis Vaccines; Mallinkrodt Veterinary; pp. 1–11.

\*\*Immucox Coccidiosis Vaccine the Natural Solution; AAP TEK Ingredients, A Divisional of Ontario Limited; pp. 1–6.

M. W. Shirley, et al.; Live Attenuated Vaccines Against Avia Coccidiosis Parasitology Today; vol. 13 No. 12 pp. 481–484 (1997).

\* cited by examiner

OVO VACCINATION AGAINST COCCIDIOSIS

RELATED APPLICATION INFORMATION

This application is a continuation of co-pending U.S. application Ser. No. 08/973,151 filed on Dec. 1, 1997 now U.S. Pat. No. 6,495,146, which claims the benefit under 35 U.S.C. §371 from PCT Application No. PCT/IB95/00445, filed Jun. 7, 1995 and published under PCT Article 21(2) in English, the disclosures of which are incorporated by reference herein in their entireties.

BACKGROUND OF THE INVENTION

The present invention relates to a method of vaccinating domesticated birds against coccidiosis. In particular, the invention relates to the in ovo administration of live Eimeria spp sporocysts or oocysts, or mixtures thereof, into the developing eggs of domesticated birds in order to immunize the hatched chicks against coccidiosis.

Coccidiosis is an enteric disease of domesticated birds caused by infection with intracellular protozoan parasites of the genus Eimeria. Coccidiosis is the most economically devastating parasitic disease of domesticated birds. It is estimated that anticoccidial medications and losses due to coccidiosis cost the poultry industry hundreds of millions of dollars every year.

Various attempts to vaccinate domesticated birds against coccidiosis have been reported since the early 1950's. Current vaccination methods include administering live Eimeria oocysts to birds through feed or water. These methods, however, are inconvenient and inefficient because not all birds get the intended oocyst dose and many are either unprotected by the vaccine or receive a pathogenic infection.

In J. M. Sharma and B. R. Burmester, Avian Dis. 26: 134–149, 1981, the authors reported that chickens vaccinated in ovo with herpesvirus of turkey developed immunity against subsequent challenge with Marek's disease virus. In European patent publication no. 291173, an immunization process is referred to wherein a nonreplicating immunogen is administered in ovo. The immunogens specifically referred to in the European patent are a genetically engineered Eimeria antigen and an Eimeria oocyst extract. The European patent specifically excludes live parasite stages such as those used in the vaccination method claimed herein.

The present vaccination method involves in ovo administration of live Eimeria sporocysts or oocysts, or a mixture thereof, into the developing eggs of domesticated birds. The available literature suggests that such a vaccination method would be ineffective in ovo and should be applied post-hatch. In T. K. Jeffers and G. E. Wagenbach, J. Parasit. 56(4): 656–662, 1970, the authors reported that in ovo injection of E. tenella sporozoites on day 10 of incubation provided no significant immunological protection against subsequent challenge with E. tenella oocysts. In fact, they reported that chicks that received no treatment had a greater survival rate against subsequent challenge with E. tenella oocysts than chicks that had been treated in ovo with sporozoites. In K. L. Watkins et al., Proc. VI th. International Coccidiosis Conf., Abstract E1-2, Ontario, Canada, 1993, the authors described in ovo inoculation with live E. maxima sporocysts and sporulated oocysts, although they did not indicate when the inoculation was done during incubation of the egg. Watkins et al. concluded that their study provided no evidence that in ovo exposure protects against subsequent coccidial challenge with E. maxima oocysts 10 days post-hatch. They also concluded that significant immunological protection is provided if inoculation is done soon after hatch rather than in ovo. Contrary to this teaching, the in ovo vaccination method of the present invention provides unexpected immunity that protects the hatched birds against subsequent coccidial challenge.

SUMMARY OF THE INVENTION

The present invention, also referred to herein as the "present vaccination method", relates to a method of vaccinating a domesticated bird against coccidiosis comprising administering in ovo, during the final quarter of incubation, an effective immunizing dose of live Eimeria sporocysts or oocysts, or a mixture thereof.

The term "domesticated bird(s)", as used herein, unless otherwise indicated, includes chickens, turkeys, ducks, game birds (including, but not limited to, quail, pheasants, and geese) and ratites (including, but not limited to, ostrich).

The term "in ovo", as used herein, unless otherwise indicated, means into a domesticated bird egg containing a live, developing embryo.

The term "administering in ovo" or "in ovo administration", as used herein, unless otherwise indicated, means administering the vaccine described herein to a domesticated bird egg containing a live, developing embryo by any means of penetrating the shell of the egg and introducing the vaccine. Such means of administration include, but are not limited to, injection of the vaccine.

The term "final quarter of incubation", as used herein, unless otherwise indicated, means the final quarter of incubation of a developing egg of a domesticated bird.

The term "Eimeria", as used herein, unless otherwise indicated, means one or more species of the genus Eimeria that infect domesticated birds. Such Eimeria species include those that are found in chicken, including E. tenella, E. acervulina, E. maxima, E. necatrix, E. mitis, E. praecox, and E. brunetti, and also those that are found in turkeys, including E. meleagrimitis, E. adenoeides, E. gallopavonis, E. dispersa, E. meleagridis, E. innocua, and E. subrotunda, and also Eimeria species that infect other domesticated birds as defined above. The term "Eimeria" also includes all strains of the foregoing species of Eimeria, including, but not limited to, precocious strains, and attenuated strains, which includes strains that have been irradiated, or otherwise treated, so that they fail to complete development. The term Eimeria also includes any newly-discovered strains or species of Eimeria that infect domesticated birds as defined above.

The term "sporocysts", as used herein, unless otherwise indicated, means live Eimeria sporocysts.

The term "oocysts", as used herein, unless otherwise indicated, means live Eimeria sporulated oocysts or a mixture of sporulated and unsporulated oocysts.

The term "effective immunizing dose", as used herein, unless otherwise indicated, means a number of sporocysts or oocysts, or, when mixed, a number of sporocysts and oocysts, sufficient to provide immunological protection in the hatched birds that is greater than the inherent immunity of non-immunized birds. As used herein, the terms "immunize" and "vaccinate" are synonymous and are used interchangeably.

A preferred dose to be administered in accord with the method of the invention comprises $10^2$ to $10^8$ sporocysts or oocysts, or a mixture thereof wherein the total number of said sporocysts and oocysts ranges from $10^2$ to $10^8$.

A more preferred dose comprises $10^2$ to $10^5$ sporocysts or oocysts, or a mixture thereof wherein the total number of said sporocysts and oocysts ranges from $10^2$ to $10^5$.

Another preferred dose comprises $10^5$ to $10^7$ sporocysts or oocysts, or a mixture thereof wherein the total number of said sporocysts and oocysts ranges from $10^5$ to $10^7$.

Another preferred dose comprises $10^4$ to $10^5$ sporocysts or oocysts, or a mixture thereof wherein the total number of said sporocysts and oocysts ranges from $10^4$ to $10^8$.

Another preferred dose comprises $10^3$ to $10^6$ sporocysts or oocysts, or a mixture thereof wherein the total number of said sporocysts and oocysts ranges from $10^3$ to $10^6$.

A preferred domesticated bird to be vaccinated in accord with the method of the invention is a chicken.

A preferred dose to be administered in ovo to chicken eggs comprises sporocysts or oocysts, or a mixture thereof, of two or more species of Eimeria selected from the group consisting of *E. tenella, E. acervulina, E. maxima, E. necatrix, E. mitis, E. praecox,* and *E. brunetti.*

Another preferred domesticated bird to be vaccinated in accord with the method of the invention is a turkey.

A preferred dose to be administered in ovo to turkey eggs comprises sporocysts or oocysts, or a mixture thereof, of two or more species of Eimeria selected from the group consisting of *E. meleagrimitis, E. adenoeides, E. gallopavonis, E. dispersa, E. meleagridis, E. innocua,* and *E. subrotunda.*

Other preferred domesticated birds to be vaccinated in accord with the method of the invention are game birds, ducks and ratites.

The method of the invention further comprises, in combination with the present vaccination method, administering in ovo an immune stimulant at any time during incubation.

A preferred method of administering the immune stimulant is simultaneously with the in ovo administration of a dose of sporocysts or oocysts, or mixture of said sporocysts and oocysts, during the final quarter of incubation.

DETAILED DESCRIPTION OF THE INVENTION

The present vaccination method involves the in ovo administration, during the final quarter of incubation, of live Eimeria sporocysts or oocysts, or a mixture thereof, into domesticated birds' eggs. In the case of chickens, in ovo administration is preferably done on days 15–20 of incubation, and most preferably on day 18 of incubation. In the case of turkeys, in ovo administration is preferably done on days 21–26 of incubation.

The present vaccination method can be performed using any suitable in ovo administration method. Preferably, the present vaccine is administered via injection. According to one method of injection, a hole is made in the egg shell at the large end of the egg using an 18 guage needle to expose the egg's air cell. A 1.0–1.5 inch 22 guage needle attached to a syringe of appropriate size (1–3 ml) can be inserted through the. hole and through the membrane of the air cell. An appropriate number of sporocysts or oocysts, or, when mixed, an appropriate number of sporocysts and oocysts, are suspended in a suitable liquid carrier, for instance 10–500 μl of phosphate-buffered saline, and then injected into the egg. The appropriate volume will depend on the size of the egg being treated, with ostrich eggs obviously being capable of taking more volume than chicken eggs. The site of injection can be within any region of the egg. Preferably, injection is done axially through the center of the large end of the egg into the amnion.

Alternatively, an automated egg injection system can be used in the present vaccination method. Such systems are described in U.S. Pat. Nos. 4,681,063, 4,040,388, 4,469,047, and 4,593,646, which are herein incorporated by reference. Other appropriate methods of injection are known to those skilled in the art.

Oocysts to be used in accord with the present vaccination method can be prepared by any of several methods known to those skilled in the art. Such methods include those described in J. F. Ryley at al., Parasitology 73:311–326, 1976 and P. L. Long et al., Folia Veterinaria Latina VI#3, 201–217, 1976, which are herein incorporated by reference. According to one method, commercial broiler chickens, approximately 2 weeks old, are infected with the Eimera species of interest by oral gavage of an appropriate dose of sporulated oocysts. For example, a typical dose used for *E. tenella* is 200,000 sporulated oocysts bird. Well known procedures for collection and purification of oocysts from infected birds are then followed. For most species of Elmeria, feces are collected from infected birds 5–7 days post-infection, blended and filtered to remove debris, then centrifuged at a speed sufficient to pellet the remaining fecal material. For *E. tenella*, a similar procedure is used except that cecal cores are taken at 6 days post-infection. The pellet is resuspended in a saturated salt solution, in which the oocysts float and most of the contaminating debris can be removed by centrifugation. The oocyst suspension is then diluted to lower the salt concentration. The oocysts are washed repeatedly to remove the salt and resuspended in potassium dichromate solution (2.5% w/v). The oocyst suspension is incubated at 29° C. with shaking (e.g., 140 rpm) for approximately 72 hours to induce sporulation of the oocysts. Alternatively, the oocysts can be treated with sodium hypochlorite and then sporulated. The number of sporulated oocysts/ml is determined by direct count using a hemocytometer, and the culture is stored, preferably under refrigeration until needed. The oocysts can be used in accord with the present vaccination method, preferably in a dose comprising from $10^2$ to $10^8$ oocysts per egg. More preferably, the dose comprises from $10^2$ to $10^5$ oocysts per egg.

To prepare sporocysts, the potassium dichromate is removed from the oocyst suspension described above by repeated washing of the oocysts, which involves collection of oocysts by centrifugation and resuspending in deionized or distilled water. When the dichromate has been removed as judged by the lack of yellowish-orange coloration, the oocyst suspension is mixed with an equal volume of sodium hypochlorite (bleach) and incubated at room temperature for 15 minutes. The bleach is then removed by repeated washings, and the oocysts are resuspended in physiological saline or deionized water. Oocysts can be broken to release sporocysts using a variety of known techniques. For example, oocysts can be broken to release sporocysts by mixing the oocysts with glass beads of 1–4 mm diameter and shaking by hand, vortex mixer, or shaking incubator, or using a hand-held homogenizer. Unbroken oocysts and oocysts walls can be separated from the released sporocysts by differential centrifugation in 50% PERCOLL, a colloidal suspension of polyvinyl pyrrolidone coated silica particles (sold by Pharmacia Biotech) or 1 M sucrose as described in Dulski et al., Avian Diseases, 32: 235–239, 1988. The sporocysts can be used in the present vaccination method either mixed with or separated from the unbroken oocysts and oocysts walls. Preferably, the dose of sporocysts is separated from the oocysts and oocysts walls. A preferred dose of sporocysts comprises from $10^2$ to $10^8$ sporocysts per egg. More preferably, the dose comprises from $10^2$ to $10^5$ sporocysts per egg.

The sporocysts or oocysts, or mixture thereof, can be injected in ovo in any physiologically suitable medium.

Preferably, they are suspended in physiologically balanced saline such as phosphate buffered saline. The selected medium can optionally include one or more suspending agents including physiologically suitable gels, gelatins, hydrosols, cellulose, or polysaccharide gums.

Preferably, in the present vaccination method, sporocysts or oocysts, or a mixture thereof, of two or more Eimeria species are injected in ovo at the same time. In accord with the present vaccination method, sporocysts or oocysts, or a mixture thereof, of all identified species of Eimeria that infect a specific domesticated bird, such as chicken, can be injected in ovo at the same time, or in series, at appropriate doses to provide immunological protection against all species.

Immune stimulants can be used in conjunction with the present vaccination method. Immune stimulants that can be used in the present vaccination method include, but are not limited to, cytokines, growth factors, chemokines, supernatants from cell cultures of lymphocytes, monocytes, or cells from lymphoid organs, cell preparations or cell extracts (e.g. fixed *Staphylococcus aureus* or lipopolysaccharide preparations), mitogens, or adjuvants, including low molecular weight pharmaceuticals. Immune stimulants can be administered in ovo at any time during incubation. Preferably, immune stimulants are administered in ovo in the medium containing the dose of Eimeria sporocysts or oocysts, or mixture thereof.

We claim:

1. A method of vaccinating a chicken against coccidiosis comprising administering in ovo, during the final quarter of incubation, an effective immunizing dose of live Eimeria oocysts, wherein the dose is administered by in ovo injection.

2. The method of claim 1 wherein the dose further comprises live Eimeria sporocysts.

3. The method of claim 1 wherein the dose is administered to the amnion.

4. The method of claim 3 wherein the dose is administered axially through the large end of the egg into the amnion.

5. The method of claim 1 wherein the dose is administered from day 15 to day 20 of incubation.

6. The method of claim 5 wherein the dose is administered on day 18 of incubation.

7. The method of claim 1 wherein the dose comprises $10^2$ to $10^8$ oocysts.

8. The method of claim 1 wherein the dose comprises $10^2$ to $10^5$ oocysts.

9. The method of claim 1 wherein the dose comprises $10^5$ to $10^7$ oocysts.

10. The method of claim 1 wherein the dose comprises $10^4$ to $10^6$ oocysts.

11. The method of claim 1 wherein the dose comprises $10^3$ to $10^6$ oocysts.

12. The method of claim 1 wherein the dose comprises oocysts of two or more species of Eimeria selected from the group consisting of *E. tenella, E. acervulina, E. maxima, E. necatrix, E. mitis, E. praecox,* and *E. brunetti.*

13. The method of claim 1 and further comprising administering in ovo an immune stimulant at any time during incubation.

14. The method of claim 13 wherein the immune stimulant is administered in ovo simultaneously with the dose of oocysts.

15. A method of vaccinating a chicken against coccidiosis comprising administering in ovo, during the final quarter of incubation, an effective immunizing dose of live Eimeria sporocysts, wherein the dose is administered by in ovo injection.

16. The method of claim 15 wherein the dose is administered to the amnion.

17. The method of claim 16 wherein the dose is administered axially through the large end of the egg into the amnion.

18. The method of claim 15 wherein the dose is administered from day 15 to day 20 of incubation.

19. The method of claim 18 wherein the dose is administered on day 18 of incubation.

20. The method of claim 15 wherein the dose comprises $10^2$ to $10^8$ sporocysts.

21. The method of claim 15 wherein the dose comprises $10^2$ to $10^5$ sporocysts.

22. The method of claim 15 wherein the dose comprises $10^5$ to $10^7$ sporocysts.

23. The method of claim 15 wherein the dose comprises $10^4$ to $10^6$ sporocysts.

24. The method of claim 15 wherein the dose comprises $10^3$ to $10^6$ sporocysts.

25. The method of claim 15 wherein the dose comprises sporocysts of two or more species of Eimeria selected from the group consisting of *E. tenella, E. acervulina, E. maxima, E. necatrix, E. mitis, E. praecox,* and *E. brunetti.*

26. The method of claim 15 and further comprising administering in ovo an immune stimulant at any time during incubation.

27. The method of claim 26 wherein the immune stimulant is administered in ovo simultaneously with the dose of sporocysts.

28. The method of claim 15 wherein the sporocysts have been purified to remove oocysts.

* * * * *